(12) United States Patent
Nifant'ev et al.

(10) Patent No.: US 6,388,118 B1
(45) Date of Patent: May 14, 2002

(54) PROCESS FOR THE PREPARATION OF CYCLOPENTADIENYL COMPOUNDS AND COMPOUNDS OBTAINED THEREFROM

(75) Inventors: Ilya E. Nifant'ev; Pavel V. Ivchenko, both of Moscow (RU)

(73) Assignee: Basell Technology Company bv, Hoofddorp (NL)

( * ) Notice: Subject to any disclaimer, the term of this patent is extended or adjusted under 35 U.S.C. 154(b) by 0 days.

(21) Appl. No.: 09/536,357

(22) Filed: Mar. 27, 2000

Related U.S. Application Data

(62) Division of application No. 08/599,475, filed on Jan. 23, 1996, now Pat. No. 6,043,403.

(30) Foreign Application Priority Data

Jan. 23, 1995 (IT) ........................................ MI95A0100

(51) Int. Cl.⁷ ............................ C07F 7/08; C07F 17/00; C07C 13/00; B01S 31/00
(52) U.S. Cl. .................... 556/465; 556/87; 556/489; 585/23; 585/502; 585/507; 585/521; 585/530; 585/638; 526/160; 526/943; 502/103; 502/117
(58) Field of Search ................................. 585/521, 502, 585/507, 530, 638, 23; 556/87, 465, 489; 502/103, 117; 526/160, 943

(56) References Cited

U.S. PATENT DOCUMENTS 5,770,755 A * 6/1998 Schertl et al. ................ 556/43

FOREIGN PATENT DOCUMENTS

| DE | 0 485 823 A1 | 1/1991 |
| EP | 0604908 A2 * | 7/1994 |

* cited by examiner

Primary Examiner—Porfirio Nazario-Gonzalez
(74) Attorney, Agent, or Firm—Bryan Cave LLP

(57) ABSTRACT

A process is disclosed for preparing bis-cyclopentadienyl compounds bridged by a single carbon atom by reacting a carbonyl compound with a cyclopentadienyl compound in the presence of a base and of an oxygen-containing solvent having an atomic ratio carbon/oxygen not higher than 3. The compounds obtainable in high yields with this simple single-step process can be used to prepare ansa-metallocenes which are active as catalyst components in the polymerization of olefins.

6 Claims, No Drawings

PROCESS FOR THE PREPARATION OF CYCLOPENTADIENYL COMPOUNDS AND COMPOUNDS OBTAINED THEREFROM

This is a divisional of U.S. application Ser. No. 08/599,475, filed Jan. 23, 1996, now U.S. Pat. No. 6,043,403.

The present invention relates to a process for preparing cyclopentadienyl compounds. More particularly, it relates to a process for preparing alkylidene-bridged bis-cyclopentadienyl compounds. The invention also relates to a class of compounds obtainable from this process.

Compounds having two cyclopentadienyl rings joined by a structural bridge are known and broadly used in the synthesis of organometallic compounds, mainly for the preparation of ansa-metallocenes which are active as catalyst components in the polymerization of olefins.

From the European application EP 129.368 are known metallocene compounds comprising cyclopentadienyl rings linked each other by a bridge constituted by an alkylene group having 1 to 4 carbon atoms. However, in said application the preparation of such compounds is not disclosed.

The European application EP 416.566 discloses propylene polymer having low molecular weight prepared by bulk polymerization carried out in the presence of a catalyst comprising (A) an alumoxane and (B) a metallocene compound in which the cyclopentadienyl rings, equal or different, are linked with a bridge having formula —R5CR6— wherein R5 and R6 can have different meanings. The ligands of the metallocene compounds are prepared by reacting a cyclopentadienyl compound, previously treated with an organo lithium compound, with a fulvene compound. If the fulvene is corresponding to the cyclopentadienyl compound, symmetric ligand can be obtained. Nevertheless, this method gives unsatisfactory yields and requires, also for the preparation of symmetric ligands, a previous step in which the fulvene is prepared and separated with consequent lowering of the whole reaction yield.

Isopropylidene-bridged cyclopentadienyl compounds have been prepared by I. E. Nifant'ev et al. in J.Chem. Research 1992, 162 by reacting a substituted cyclopentadienyl compound with 6,6-dimethylfulvene in the presence of a NaOH\THF system. Also in this case the 6,6-dimethylfulvene is separately prepared. Furthermore, since the 6,6-dimethylfulvenes having substituents on the cyclopentadienyl ring do not react in these conditions it is impossible to obtain isopropylidene-bridged bis-cyclopentadienyl compounds having substituents on the cyclopentadienyl ring.

According to the same author in Organometallics 1991, 10, 3739, isopropylidene-bis(cyclopentadiene) is prepared by only one step reacting cyclopentadiene and acetone in the presence of the system NaOH\THF. The yields obtained are about 60%. However, in these conditions substituted cyclopentadienes do not react with acetone.

I. F. Urazowski et al. at the Xth Fechem Conference on Organometallic Chemistry held on Sep. 5–10, 1993 in Agia Pelagia, Crete—Greece, presented metallocene complexes of Ti and Zr obtained from two dicyclopentadienyl-dimethyl-methanes, namely those having an isopropyl or tertbutyl substituent on the 3-position of each cyclopentadienyl ring. However, only mechanisms of the formation of those complexes and their structural features on the basis of X-ray analysis were discussed, whilst the preparation of the corresponding dicyclopentadienyl-dimethyl-methanes was not described.

Therefore, it would be highly desirable to provide an easy and advantageous route to the preparation of the general class of bis-cyclopentadienyl compounds bridged by a single carbon atom.

The applicant has now surprisingly found that, by operating under particular conditions, alkylidene-bridged bis-cyclopentadienyl compounds having substituents on the cyclopentadienyl rings can be prepared by means of an easy one-step process.

Therefore, it is an object of the present invention a process for preparing symmetric bridged bis-cyclopentadienyl compounds having the general formula (I):

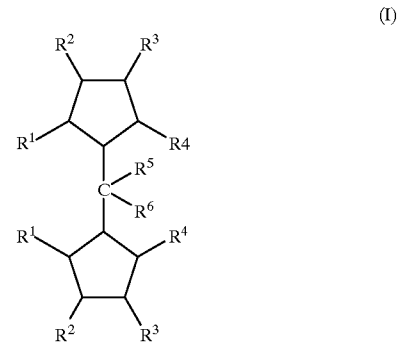

(I)

wherein the double bonds of the cyclopentadienyl ring can be in any of the allowed positions wherein $R^1$, $R^2$, $R^3$ and $R^4$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals which can contain atoms of Si or Ge, and furthermore two adjacent $R^1$, $R^2$, $R^3$ and $R^4$ substituents on the same cyclopentadienyl ring can form a ring having 5 to 8 carbon atoms;

$R^5$ is a hydrogen atom or a —$CHR^7R^8$ group;

$R^6$ is a $C_6$–$C_{20}$-aryl radical or a —$CHR^9R^{10}$ group;

$R^7$, $R^8$, $R^9$ and $R^{10}$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals which can contain hetero atoms such as nitrogen, phosphorus, oxygen or sulphur, or two $R^7$, $R^8$, $R^9$ and $R^{10}$ substituents can form a ring having 3 to 8 carbon atoms, which can also contain hetero atoms;

said process comprising the reaction of a carbonyl compound of formula (II):

(II)

wherein $R^5$ and $R^6$ have the meaning given above, with a cyclopentadienyl compound of formula (III):

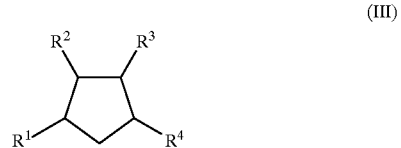

(III)

wherein the double bonds in the cyclopentadienyl rings can be in any of the allowed positions wherein $R^1$, $R^2$, $R^3$ and $R^4$ have the meaning given above, said reaction being carried out in the presence of a base and of an oxygen-containing solvent having an atomic ratio carbon/oxygen not higher than 3.

The double bonds of the cyclopentadienyl rings in the compounds of formula (I) and (III) can be in any of the allowed positions.

The choice of the solvent is critical for the invention. Unsuitable solvents will not give the desired final product, or will give it with unsatisfactory yields.

A particularly suitable class of solvents for use in the process of the invention are the polyethers such as, for example:

diethers, such as dimethoxyethane, diethoxyethane, triethers, such as diglyme, crown ethers, mono-, di-, oligo- or polyethyleneglycole.

Examples of bases suitable for use in the process of the present invention are, for instance, the alkali or alkali earth metal hydroxides, such as lithium hydroxide, sodium hydroxide, potassium hydroxide, calcium hydroxide, barium hydroxide. Potassium hydroxide is the preferred.

According to a particularly preferred embodiment, the process of the invention is carried out in the presence of the system consisting of potassium hydroxide and dimethoxyethane.

The reaction temperature is generally comprised between −50° C. and the boiling temperature of the solvent.

The time of the reaction can vary in a wide range. Generally it is comprised between 2 minutes and 24 hours, more typically between 30 minutes and 4 hours.

In the above reaction, the molar ratio of the cyclopentadienyl compound (III) to the carbonyl compound (II) can vary in a very wide range and, in dependence of said (III)/(II) molar ratio, different embodiments can be practised which permit to obtain the desired final products. Each of said embodiments permits to obtain a different type of final products. However, the above molar ratio is generally equal to or lower than 2.

According to a preferred embodiments of the process of the invention, the reaction between the cyclopentadienyl compound (III) and the carbonyl compound (II) is conducted with a molar ratio (III)/(II) of about 2:1. When such a ratio is used, in dependence of the choice of the type and the number of the substituents in the formulae (II) and (III), different alkylidene-bridged bis-cyclopentadienyl compounds can be prepared in a single step.

Accordingly, starting from cyclopentadienyl compounds of formula (III) in which at least one of the $R^1$, $R^2$, $R^3$ and $R^4$ substituents is a $C_1$–$C_{10}$ alkyl group, compounds belonging to the class of the alkylidene-bridged bis(alkyl-substituted-cyclopentadienyl) compounds can be obtained, in yields generally higher than those of the processes of the prior art.

In particular when, operating at a (III)/(II) molar ratio of about 2:1, acetone is employed as the carbonyl compound of formula (II) and an alkyl-substituted cyclopentadienyl compound as the compound of formula (III), bridged bis-alkyl-substituted-cyclopentadienes of formula (IV):

2,2-bis(CpR'$_n$H$_{4-n}$)propane  (IV)

in which R' is a $C_1$–$C_{10}$ alkyl radical like methyl, ethyl, isopropyl, t-butyl and the like, and n is an integer comprised between 1 and 4, can be obtained in a single step with yields higher than 75%. In the case of 2,2-bis(monoalkyl-cyclopentadienyl)propanes, the NMR spectra show that the alkyl substituents are connected with the β-carbon atom of the cyclopentadienyl ring. Examples of compounds of formula (IV) are:

2,2-bis(3-methyl-cyclopentadienyl)propane,
2,2-bis(3-ethyl-cyclopentadienyl)propane,
2,2-bis(3-isopropyl-cyclopentadienyl)propane,
2,2-bis(3-t-butyl-cyclopentadienyl)propane,
2,2-bis(2,4-diethyl-cyclopentadienyl)propane,
2,2-bis(2-methyl-4-isopropyl-cyclopentadienyl)propane,
2,2-bis(2-methyl-4-t-butyl-cyclopentadienyl)propane,
2,2-bis(2,3,4,5-tetramethyl-cyclopentadienyl)propane,
2,2-bis(2,3,4,5-tetraethyl-cyclopentadienyl)propane.

Another class of compounds which is possible to obtain in a single step, operating at a (III)/(II) molar ratio of about 2:1 is that of alkylidene-bridged bis-indenyl compounds. These compounds are obtainable by starting from compounds of formula (III) in which the $R^1$ and $R^2$ substituents or the $R^3$ and $R^4$ substituents form a benzene ring, that is indenyls or substituted indenyl compounds.

In this class of alkylidene-bridged bis-indenyl compounds, particularly preferred are the 2,2-bis(indenyl) propanes which can be obtained by reacting indenyl compounds with acetone in the presence of a suitable alkali/solvent system such as KOH/DME. Examples of such compounds are:

2,2-bis(indenyl)propane,
2,2-bis(3-methyl-indenyl)propane,
2,2-bis(3-ethyl-indenyl)propane,
2,2-bis(3-isopropyl-indenyl)propane,
2,2-bis(3-t-butyl-indenyl)propane,
2,2-bis(4,7-dimethyl-indenyl)propane.

Moreover, substituted bridged bis-indenyl compounds can be prepared by a post-treatment of the 2,2-bis(indenyl) propane obtained according to the above embodiment. For example, 2,2-bis(3-trimethylsilyl-indenyl)propane can be obtained by treating the dilithium salt of 2,2-bis(indenyl) propane with trimethylchlorosilane.

Examples of bis-cyclopentadienyl compounds bridged with a group other that isopropylidene, obtainable with the process of the invention are:

1,1-bis(cyclopentadienyl)cyclopentane,
1,1-bis((1H)inden-3-yl)cyclopentane,
1,1-bis(cyclopentadienyl)cyclohexane,
1,-bis((1H)inden-3-yl)cyclohexane,
1,1-bis(cyclopentadienyl)cycloheptane,
1,1-bis((1H)inden-3-yl)cycloheptane,
1,1-bis(cyclopentadienyl)cyclopropylethane,
1,1-bis((1H)inden-3-yl)cyclopropylethane,
bis(cyclopentadienyl)phenylmethane,
bis(indenyl)phenylmethane,
4,4-bis-cyclopentadienyl-1-methyl-piperidine.
4,4-bis-indenyl-1-methyl-piperidine.

According to another embodiment of the invention, the carbonyl compound of formula (II) can be used in excess with respect to the stoichiometric molar ratio (III)/(II) of 2:1. In particular, the molar ratio (III)/1(II) can be of about 2:3.

In such conditions, cyclopentadienyl compounds of formula (I) having alkylidene substituents in the β-position on the cyclopentadienyl ring can be obtained as main products of the reaction.

If the carbonyl compound of formula (II) is employed in great excess, it can be used as the reaction solvent.

Therefore, it is another object of the present invention a process for preparing bridged cyclopentadienyl compounds having the general formula (VI):

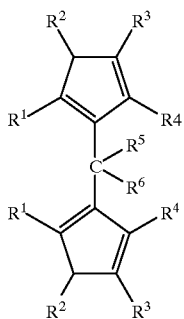

(VI)

wherein $R^1$, $R^3$, $R^4$, $R^5$, and $R^6$ have the meaning given above, and the $R^2$ substituents, which can be identical or different, are alkylidene radicals of formula (V):

(V)

wherein $R^5$ and $R^6$ have the meaning given above, said process comprising the reaction of a carbonyl compound of formula (II):

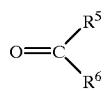

(II)

wherein $R^5$ and $R^6$ have the meaning given above, with a cyclopentadienyl compound of formula (III):
as reported above
wherein $R^1$, $R^2$, $R^3$ and $R^4$ have the meaning given above, in a molar ratio (II)/(III) equal or higher than 1.5, said reaction being carried out in the presence of a base.

For example, when the reaction between indene and acetone is carried out with molar ratio indene:acetone of about 2:3, or with an excess of acetone employing acetone as reaction solvent, the compound obtained is 2,2-bis(3-benzo-6,6-dimethyl-fulvene)propane. This is a very versatile compound which can be transformed, according to well known reaction, in various 2,2-bis(indenyl)propanes with substituents in the 3-position of the indenyl groups.

For example, 2,2-bis(3-benzo-6,6-dimethyl-fulvene) propane can be reacted in a suitable solvent with hydrides, such as LiH or LiAlH4, or metallorganic compound, such as LiMe, to obtain respectively 2,2-bis(3-isopropyl-indenyl) propane or 2,2-bis(3-t-butyl-indenyl)propane directly in the anionic form to be in turn converted in the metallocene compound.

The bridged cyclopentadienyl compounds obtained from the reaction between the carbonyl compound of formula (II) and the cyclopentadienyl compound of formula (III) according to the present invention, are recovered and separated from the reaction mixture by the known technique such as extraction, crystallization, distillation, chromatography etc.

The alkylidene-bridged bis-cyclopentadienyl compounds obtainable by the process of the present invention can be employed to prepare the corresponding metallocene compounds with transition metals such as titanium, zirconium of hafnium, which are useful as catalytic components in the polymerization of olefins.

Some of the alkylidene-bridged bis-cyclopentadienyl compounds obtainable with the process of the present invention are not known at the date of the present invention. Therefore, it is a further object of the present invention a bridged cyclopentadienyl compound having the general formula (I):

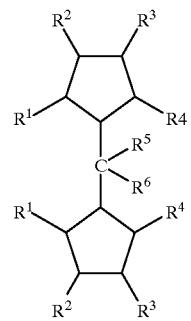

(I)

wherein the double bonds of the cyclopentadienyl rings can be in any of the allowed positions, wherein $R^1$, $R^2$, $R^3$, $R^4$, $R^5$ and $R^6$ are defined as above, with the proviso that, when the $R^5$ and the $R^6$ substituents are methyl groups, the following conditions apply:
at least one of the $R^1$, $R^2$, $R^3$ and $R^4$ substituents is different from a hydrogen atom,
if the $R^1$, $R^2$ and $R^4$ substituents are hydrogen atoms, the $R^3$ substituents are other than isopropropyl or tertbutyl groups, and
the two bridged ligands are other than unsubstituted indenyls.

Particularly interesting new bis-cyclopentadienyl compounds of formula (I) obtainable from the process of the invention are those in which the $R^3$ substituents are carbon, silicon or germanium atoms substituted with three alkyl, cycloalkyl, aryl, alkylaryl or arylalkyl groups having 1 to 10 carbon atoms, and wherein the $R^4$ substituents are hydrogen atoms. Examples of such compounds are:
2,2-bis(3-t-butyl-cyclopentadienyl)propane,
2,2-bis(2-methyl-4-t-butyl-cyclopentadienyl)propane,
2,2-bis(3-t-butyl-indenyl)propane,
2,2-bis(3-trimethylsilyl-indenyl)propane.

The following examples are given for illustrative purposes and do not limit the invention.

CHARACTERIZATIONS

The $^1$H-NMR and $^{13}$C-NMR analyses were carried out on a Varian 300 MHz instrument, using $CDCl_3$ as a solvent, at room temperature.

All the operations were carried out in a dry nitrogen atmosphere, using the conventional techniques for the handling of compounds which are sensitive to air.
THF=tetrahydrofuran
Et$_2$O=ethyl ether
DME=dimethoxyethane

EXAMPLE 1

Synthesis of 2,2-bis(indenyl)propane 23.5 ml (200 mmol) of indene was added within 0.5 hours to a suspension of 15 g of milled KOH in 150 ml of DME.

The mixture was heated to reflux. Then 7.5 ml (100 mmol) of acetone was added dropwise within 0.5 hours and the mixture was stirred under reflux for additional 2 hours. The resulting mixture was cooled, treated with 200 ml of diluted phosphoric acid until neutralization and then with 100 ml of diethyl ether. The organic layer was separated, washed with water and dried over $Na_2SO_4$. Then the solvent was removed in vacuo and the residue was distilled at 130–160° C. and 0.01 torr. The broad fraction was collected and recrystallized from a 1:1 ether/hexane mixture, thus obtaining 20.4 g of the product (yield 72%). $^1$H-NMR (acetone-$d_8$, 30° C.) δ: 7.37 (d,2H); 7.32 (d,2H); 6.98 (m,4H); 6.60 (t,2H)) {═CH—} 3.38 (d,4H, —$CH_2$—) 1.74 (s,6H, —$CH_3$).

EXAMPLE 2

Synthesis of 2,2-bis(3-methyl-indenyl)propane

It was worked according to the procedure described in example 1 except that, instead of indene, 200 mmol of 3-methyl-indene was used and that, after the acetone addition, the mixture was stirred under reflux for 3 hours. The temperature of distillation was 135–165° C. The product was isolated as dilithium salt (yield 65%). $^1$H-NMR (THF-$d_8$, 30° C.) δ: 7.42 ("d",2H); 7.10 ("d",2H); 6.26 ("t",2H); 6.18 ("t",2H) {ABCD, J=9 Hz} 6.47 (s,2H); 2.33 (s,6H,Ind-$CH_3$); 1.90 (s,6H,>$CMe_2$).

EXAMPLE 3

Synthesis of 2,2-bis(3-isopropyl-indenyl)propane

It was worked according to the procedure described in example 1 except that, instead of indene, 200 mmol of 3-isopropyl-indene was used and that, after the acetone addition, the mixture was stirred under reflux for 4 hours. The temperature of distillation was 140–175° C. The product was isolated as dilithium salt (yield 63%). $^1$H-NMR (THF-$d_8$, 30° C.) δ: 7.45 ("d",2H) 7.27 ("d",2H) 6.30 ("t",2H) 6.23 ("t",2H) {ABCD, J=8.0 HZ} 6.63 (s,2H) 3.30 (sept, J=7.0 Hz,2H,—C$\underline{H}$($CH_3$)$_2$); 1.98 (s, 6H,>$CMe_2$) 1.35 (d,J=7.0 Hz, 12H, —CH(C$\underline{H}_3$)$_2$).

EXAMPLE 4

(a) Synthesis of 2,2-bis(3-benzo-6,6-dimethyl-fulvene) propane

It was worked according to the procedure described in example 1 but employing 300 mmol of acetone. 26.1 g of product was obtained (yield 73%).

(b) Synthesis of 2,2-bis(3-isopropyl-indenyl)propane

A solution of 6.27 g (17.8 mmol) of 2,2-bis(3-benzo-6, 6-dimethyl-fulvene)propane in 100 ml THF was treated with 0.68 g of $LiAlH_4$ (2× excess) at −20° C. The mixture was allowed to warm to room temperature and refluxed for 5 hours. The resulting solution was poured into 200 ml of $H_2O$, neutralized and extracted with 2×50 ml of $Et_2O$. The organic layer was dried, the solvent was removed, and the residue was dried in vacuo. 4.16 g of the product was isolated and used without further purification in the next step (yield 63.4%).

EXAMPLE 5

Synthesis of 2,2-bis(3-tertbutyl-indenyl)propane

It was worked according to the procedure described in example 1 except that, instead of indene, 200 mmol of 3-tertbutyl-indene was used and that, after the acetone addition, the mixture was stirred under reflux for 4 hours. The temperature of distillation was 145–185° C. The product was isolated as dilithium salt (yield 48%). $^1$H-NMR (THF-$d_8$, 30° C.) δ: 8.17 ("t",4H) 6.95 (mm,4K) {ABCD} 7.36 (s,2H) 2.70 (s,6H,>$CMe_2$) 2.19 (s, 18H,—$CMe_3$).

EXAMPLE 6

Synthesis of 2,2-bis(3-t-butyl-cyclopentadienyl) propane 10 g of KOH 150 mmol of t-butyl-cyclopentadiene and 4.35 g of acetone were suspended in 100 ml of DME and the mixture obtained was heated to reflux and stirred for 2 hours. The mixture was then cooled and treated with 200 ml of water and 100 ml of diethyl ether. The organic phase was separated off, washed with water and dried over $CaCl_2$. The solvent was then evaporated in vacuo and the residue was distilled at a temperature of 145–165° C. The broad fraction was collected and recrystallized (yield 81%). $^1$H-NMR ($CDCl_3$) δ: 6.3–5.7 (m, 4H) 3.0–2.8 (m, 4H) 1.5–b 1.4 (m, 6H) 1.3–1.2 (m, 18H).

EXAMPLE 7

Synthesis of 2,2-bis(2-methyl-4-t-butyl-cyclopentadienyl)propane 17.8 g (131 mmol) of 2-methyl-4-t-butyl-cyclopentadiene was added within 0.5 hours under vigorous stirring to a suspension of 10 g of KOH powder in 100 ml of DME. The obtained mixture was heated to reflux. Then 4.8 ml (66 mmol) of acetone was added dropwise within 0.5 hours and the mixture was stirred under reflux for additional 6 hours. The resulting mixture was cooled, treated with 200 ml of diluted phosphoric acid until neutralization and then with 100 ml of diethyl ether. The organic layer was separated, washed with water and dried over $Na_2SO_4$. Then the solvent was removed in vacuo and the residue was distilled under 0.01 torr. The 130–160° C. broad fraction was collected, diluted with 30 ml of $Et_2O$ and treated with 60 ml of a 2.0M solution of n-butyllithium in hexane. White crystalline precipitate of the product was isolated as the dilithium salt, washed twice by 20 ml of $Et_2O$ and dried in vacuo (yield 60%). $^1$H-NMR (THF-$d_8$, 30° C.)) δ: 5.52 ("d", 2H); 5.22 ("d", 2H); 3.58 (s, 6H); 1.58 (s, 6H); 1.18 (s, 18H).

EXAMPLE 8

Synthesis of 1,1-bis((1H)inden-3-yl)cyclopentane 15 g of the milled KOH and 23.5 ml (200 mmol) of indene were suspended in 150 ml of DME and the mixture was heated till the reflux. Then 7.5 ml (100 mmol) of cyclopentanone was added dropwise within 0.5 hours and the mixture was stirred under reflux in additional 2 hours. After that, the mixture was cooled, treated by 200 ml of water and by 100 ml of diethyl ether. The organic layer was separated, washed by water and dried over $CaCl_2$. Then the solvent was removed in vacuo and the residue was distilled. The broad fraction 180–240° C./00.1–0.02 torr was collected. The product obtained (18.5 g) was recrystallized from heptane (yield 62%).

EXAMPLE 9

Synthesis of 1,1-bis((1H)inden-3-yl)cyclohexane 15 g of the milled KOH and 23.5 ml (200 mmol) of indene were suspended in 150 ml of DME and the mixture was heated till the reflux. Then 9.3 ml (100 mmol) of cyclohexanone was added dropwise within 0.5 hours and the mixture was stirred under reflux in additional 2 h. After that, the mixture was cooled, treated by 200 ml of water and by 100 ml of diethyl ether. The organic layer was separated, washed by water and dried over $CaCl_2$. Then the solvent was removed in vacuo and the residue was distilled. The broad fraction 190–240° C./0.02 torr was collected. The product obtained (23.7 g) was recrystallized from heptane (yield 76%).

EXAMPLE 10

Synthesis of 1,1-bis((1H)inden-3-yl)cycloheptane 15 g of the milled KOH and 23.5 ml (200 mmol) of indene were suspended in 150 ml of DME and the mixture was heated till the reflux. Then 10.67 ml (100 mmol) of cyclopentanone was added dropwise within 0.5 hours and the mixture was stirred under reflux in additional 2 hours. After that, the mixture was cooled, treated by 200 ml of water and by 100 ml of diethyl ether. The organic layer was separated, washed with water and dried over $CaCl_2$. Then the solvent was removed in vacuo and the residue was distilled. The broad fraction 190–240° C./0.02 torr was collected. The product obtained (22.2 g) was recrystallized from heptane (yield 68%).

EXAMPLE 11

Synthesis of 1,1-bis((1H)inden-3-yl)-1-cyclopropylethane 15 g of the milled KOH and 23.5 ml (200 mmol) of indene were suspended in 150 ml of DME and the mixture was heated till the reflux. Then 8.6 ml (100 mmol) of acetylcyclopropane was added dropwise within 0.5 hours and the mixture was stirred under reflux in additional 3 hours. After that, the mixture was cooled, treated by 200 ml of water and by 100 ml of diethyl ether. The organic layer was separated, washed by water and dried over $CaCl_2$. Then the solvent was removed in vacuo and the residue was distilled. The broad fraction 180–230° C./0.02 torr was collected. The product obtained (21.8 g) was recrystallized from heptane (yield 73%).

EXAMPLE 12

Synthesis of bis(indenyl)phenylmethane

It was worked according to the procedure described in example 1 except that, instead of acetone, 100 mmol of benzaldeide was used and that, after the benzaldeide addition, the mixture was stirred under reflux for 5 hours. The temperature of distillation was 140–170° C. The collected fraction was recrystallized from a heptane (yield 60%). $^1$H-NMR (acetone-$d_6$, 30° C.) δ: 7.52–7.18 {mm, 13H,} 6.05 (q,2H,=CH—) 5.39 (m,1H,>CH—) 3.40 (br.s., 4H,—CH$_2$—). $^{13}$C—NMR (CD$_2$Cl$_2$, 30° C.) δ145.6; 145.1; 141.5 (=C<) 131.8; 129.3; 128.7; 127.0; 126.2; 124.1; 120.2 (=CH—) 44.5 (>CH—) 38.1 (—CH$_2$—).

EXAMPLE 13

Synthesis of 2,2-bis(3-benzo-6,6-dimethyl-fulvene)propane 38.7 g (0.330 mol) of indene, 155 ml (2.11 mol) of acetone and 2.71 g of KOH were placed in a 250 ml flask under a nitrogen atmosphere. The resulting solution was stirred in dark for 15 days, then its colour became green and a yellow solid product crystallized on the bottom of the flask. The solid was collected, washed with water, dissolved in $CH_2Cl_2$ filtered and dried over $Na_2SO_4$. After elimination of the solvent, the yellow solid was recrystallized from pentane. 5.53 g of pure 2,2-bis(3-benzo-6,6-dimethyl-fulvene)propane was thus obtained.

EXAMPLE 14

Synthesis of 2,2-bis(3-trimethylsilyl-indenyl)propane 5.45 g (20 mmol) of 2,2-bis(indenyl)propane prepared according to the procedure of example 1 was dissolved in 100 ml of ether. The solution thus obtained was taken to –20° C., and 22 ml of a 2.0 M solution of n-butyl-lithium in pentane was added, thus giving a suspension of dilithium-2,2-bis(indenyl)propane. 8.77 g (30.85 mmol) of dilithium 2,2-bis(indenyl)propane was dissolved in 100 ml of ether, and 10 ml of Me$_3$SiCl (excess) was added at a temperature of –40° C. The resulting mixture was allowed to return to room temperature. The organic phase was then separated off, the solvent removed and the product dried in vacuo. $^1$H-NMR

EXAMPLE 15

Synthesis of 4,4-bis-indenyl-1-methyl-piperidine 0.25 mole of indene was added within 0.5 hours under vigorous stirring to the suspension of 15 g of KOH powder in 150 ml of DME. The mixture was heated to reflux. Then 0.1 mole of 1-methylpiperidone dissolved in 10 ml of DME was added dropwise within 0.5 hours and the mixture was stirred under reflux for additional 2 hours. The resulting mixture was cooled, treated by 200 ml of diluted phosphoric acid till the neutralization and by 100 ml of Et$_2$O. The organic layer was separated and treated by 20% excess of diluted acetic acid. The aqueous layer was separated, washed twice with Et$_2$O and neutralissed with a diluted alkali solution. The 4,4-bis-indenyl-1-methyl-piperidine was extracted with $CH_2Cl_2$, the organic layer was separated, the solvent was removed and the residue was recrystallized from hexane. The yield of the 4,4-bis-indenyl-1-1methyl-piperidine was 67%. $^1$H NMR (C$_6$D$_6$, 30° C.) δ: 7.57(d,2H); 7.20(d,2H); 7.04(t,2H); 6.97(t,2H); 6.28(s,2H); 3.08(s,4H); 2.58(m,4H); 2.44(m,4H); 2.17(s,3H).

What is claimed is:

1. A bridged cyclopentadienyl compound having the general formula (I):

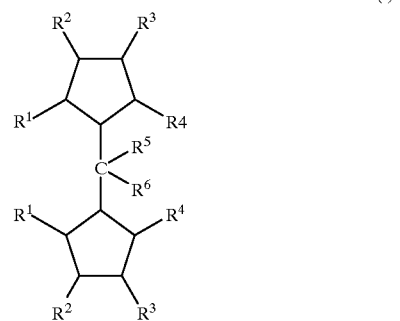

wherein the double bonds in the cyclopentadienyl rings can be in any of the allowed positions, wherein $R^1$, $R^2$, $R^3$, and $R^4$ can be identical or different from each other, but wherein the two $R^1$ groups are the same as each other, the two $R^2$ groups are the same as each other, the two $R^3$ groups are the same as each other, and the two $R^4$ groups are the same as each other, the $R^1$, $R^2$, $R^3$, and $R^4$ groups being selected from the group consisting of hydrogen atoms, $C_1$–$C_{20}$-alkyl, $C_2$–$C_{20}$-alkenyl, $C_3$–$C_{20}$-cycloalkyl, $C_6$–$C_{20}$-aryl, $C_7$–$C_{20}$ alkylaryl, or $C_7$–$C_{20}$-arylalkyl radicals, each of which can contain atoms of Si or Ge, and furthermore two adjacent $R^1$, $R^2$, $R^3$, and $R^4$ substituents on the same cyclopentadienyl ring can form a ring having 5 to 8 carbon atoms;

$R^5$ is a hydrogen atom or a —$CHR^7R^8$ group;

$R^6$ is a $C_6$–$C_{20}$-aryl radical or a —$CHR^9R^{10}$ group;

$R^7$, $R^8$, $R^9$, and $R^{10}$, which can be identical or different, are hydrogen atoms or $C_1$–$C_{20}$-alkyl, $C_2$–$C_{20}$-alkenyl, $C_3$–$C_{20}$-cycloalkyl, $C_6$–$C_{20}$-aryl, $C_7$–$C_{20}$ alkylaryl, or $C_7$–$C_{20}$-arylalkyl radicals, each of which can contain heteroatoms, or two $R^7$, $R^8$, $R^9$, and $R^{10}$ substituents can form a ring having 3 to 8 carbon atoms;

wherein each group of carbon atoms represented by a five-member ring in formula (I) and their attached substituents are called "bridged ligands";

wherein when the $R^5$ and $R^6$ substituents are methyl groups, one of following conditions applies:
  at least one of the $R^1$, $R^2$, $R^3$, and $R^4$ substituents is different from hydrogen, or
  if the $R^1$ and $R^4$ substituents are hydrogen atoms, the $R^3$ substituents are other than isopropyl or tert-butyl groups, or
  the two bridged ligands are other than unsubstituted indenyls, or
  the two bridged ligands are other than 2-methyl-inden-1-yl, 3-isopropyl-inden-1-yl, 3-tert-butyl-inden-1-yl, 4-tert-butyl-fluoren-9-yl, and fluoren-9-yl groups.

2. The bridged cyclopentadienyl compound according to claim 1, wherein at least one of the $R^1$, $R^2$, $R^3$, and $R^4$ substituents contains one or more atoms of Si or Ge.

3. The bridged cyclopentadienyl compound according to claim 1, wherein at least one of the $R^7$, $R^8$, $R^9$, and $R^{10}$ substituents contains one or more hetero atoms.

4. The bridged cyclopentadienyl compound according to claim 3, wherein at least one of the $R^7$, $R^8$, $R^9$, and $R^{10}$ substituents contains a hetero atom selected from the group consisting of nitrogen, oxygen, phosphorous, and sulfur.

5. The bridged cyclopentadienyl compound according to claim 1, wherein the $R^3$ substituents are carbon, silicon, or germanium atoms substituted with three alkyl, cycloalkyl, aryl, alkylaryl, or arylalkyl groups having 1 to 10 carbon atoms, and the $R^4$ substituents are hydrogen atoms.

6. The bridged cyclopentadienyl compound according to claim 1, wherein the bridged cyclopentadienyl compound is selected from the group consisting of 2,2-bis(2-methyl-4-t-butyl-cyclopentadienyl)propane, 2,2-bis(3-t-butyl-indenyl)propane), and 2,2,-bis(3-trimethylsilyl-indenyl)propane.

* * * * *